(12) United States Patent
Linstrom

(10) Patent No.: US 11,654,058 B2
(45) Date of Patent: May 23, 2023

(54) BIB SHAPED BANDAGE

(71) Applicant: John E. Linstrom, Polson, MT (US)

(72) Inventor: John E. Linstrom, Polson, MT (US)

( * ) Notice: Subject to any disclaimer, the term of this patent is extended or adjusted under 35 U.S.C. 154(b) by 312 days.

(21) Appl. No.: 16/858,679

(22) Filed: Apr. 26, 2020

(65) Prior Publication Data

US 2021/0330511 A1 Oct. 28, 2021

(51) Int. Cl.
*A61F 13/00* (2006.01)
*A61F 13/10* (2006.01)
*A61F 13/06* (2006.01)

(52) U.S. Cl.
CPC ...... *A61F 13/105* (2013.01); *A61F 13/00063* (2013.01); *A61F 13/063* (2013.01); *A61F 13/068* (2013.01); *A61F 2013/0048* (2013.01); *A61F 2013/0091* (2013.01); *A61F 2013/0094* (2013.01); *A61F 2013/00608* (2013.01); *A61F 2013/00646* (2013.01); *A61F 2013/00655* (2013.01)

(58) Field of Classification Search
CPC .............. A61F 13/105; A61F 13/00063; A61F 13/063; A61F 13/068; A61F 2013/0048; A61F 2013/00608; A61F 2013/00646; A61F 2013/00655; A61F 2013/0091; A61F 2013/0094

See application file for complete search history.

(56) References Cited

U.S. PATENT DOCUMENTS

| | | | | |
|---|---|---|---|---|
| 2,827,049 | A * | 3/1958 | Scholl | A61F 13/063 128/894 |
| 5,968,536 | A * | 10/1999 | Godfrey | A61F 13/064 424/443 |
| 2010/0168632 | A1 * | 7/2010 | Abbassian | A61F 13/068 128/893 |
| 2013/0253400 | A1 * | 9/2013 | Massa | A61F 13/105 602/22 |
| 2020/0008983 | A1 * | 1/2020 | Linstrom | A61F 13/00063 |

* cited by examiner

*Primary Examiner* — Steven O Douglas

(57) ABSTRACT

A bandage intended for use on digits; i.e. fingers and toes, to cover injuries to the knuckle or pad area of the first joint on the hand or foot. The bandage is configured as a pad with an angled loop, the loop used as an anchor around the base of a digit in order to resist motions that might peel the bandage off the skin. The pad may contain medicines suitable for treating a wound or injury, may be radio opaque, may contain a reinforced surface to prevent compression or skin friction at the site, or other ancillary devices. The loop is deformable in length in order to fit different digits and wound locations.

8 Claims, 2 Drawing Sheets

Outer-facing Surface

Side View

Skin-facing Surface

Bottom View

BIB SHAPED BANDAGE

BACKGROUND

The human digits we call fingers and toes can be difficult to bandage. In normal use these joints flex, stretch and change shape, they protrude and rotate. The joint where the digit joins the body is the most difficult joint to keep bandaged. A usual solution is an adhesive bandage, similar to those bandages used on other parts of the body. The most commonly available bandages resemble circles, strips or a capital H.

Bandage failures in the adhesive usually cause it to peel off the skin and release whatever tension it provided to keep a bandage pad in place. This failure is usually at an edge of the adhesive sheet rather than toward the center and usually at a sharper curve than along a straighter edge. In engineering this sharper curve is called a stress riser and here is where any outside pressure is more likely to cause a failure. This sharper curve can be any adhesive shape that extends away from the adhesive shape near the bandage pad. These sharper curves are a common point of failure because any sharper curve that can be wrapped around a digit can be unwrapped more easily than a place on a straighter edge. Consider the spot bandage: it has no sharper curve areas, but the bandage must be large and subsequently inhibiting to digit movement or to resist peeling. A strip bandage has two sharper curves. The capital H style has four.

After a knuckle or its associated pad is bandaged, normal human actions like making a fist, putting on socks or gloves or reaching into pockets can ruin the effort. Better adhesives and more flexible bandages may help but a better solution involves replacing the adhesive tabs, those sharper curves, with what they add to the bandage-anchor points, while removing their adhesive weakness. Each adhesive tab is under tension to hold the bandage pad in place. The tension on two anchor tabs is the same as on one continuous anchor tag stretched from the first bandage pad location, around anchor joint and back to the second bandage pad location.

SUMMARY

As a solution to the failing adhesive arms of a bandage, the shape of a bandage similar to a bib is described. This bandage shape consists of the bandage pad and a one piece anchor loop. The anchor loop is placed over the digit whose knuckle or pad is to be bandaged. The loop replaces the two bandage tabs and provides tension without adhesive failure. For anatomical comfort, much as a fitted sock is more comfortable than tube sock, an angled loop is presented as a preferred embodiment. Due to different body shapes and sizes, the loop can be sized to fit different hands and feet or it can be made to accommodate a range of sizes with a stretchable loop. A loop made of low density polyethylene, for example, remains at the length it was stretched; no elastic rebound or creeping stretch. For the rest of this document, this characteristic for any suitable material shall be abbreviated as 'deformable.' The loop connects to the bottom end of the bandage pad and it's shape and cross-section are driven by its needed strength, the digit's comfort and conformability around the digit. A dressing may be added in the central area of the bandage pad. Layers between the inner and outer layers may be added for purpose and a sterile pad cover and handling tab may be added over the inner layer that faces the skin.

DESCRIPTION OF THE DRAWINGS

The drawings depict several views of an embodiment of the disclosed bandage. Together with the detailed description, these drawings will explain the various parts and functions of the disclosure. Refer to the following drawings to understand the applications, features and use of this bandage.

Figure 1:
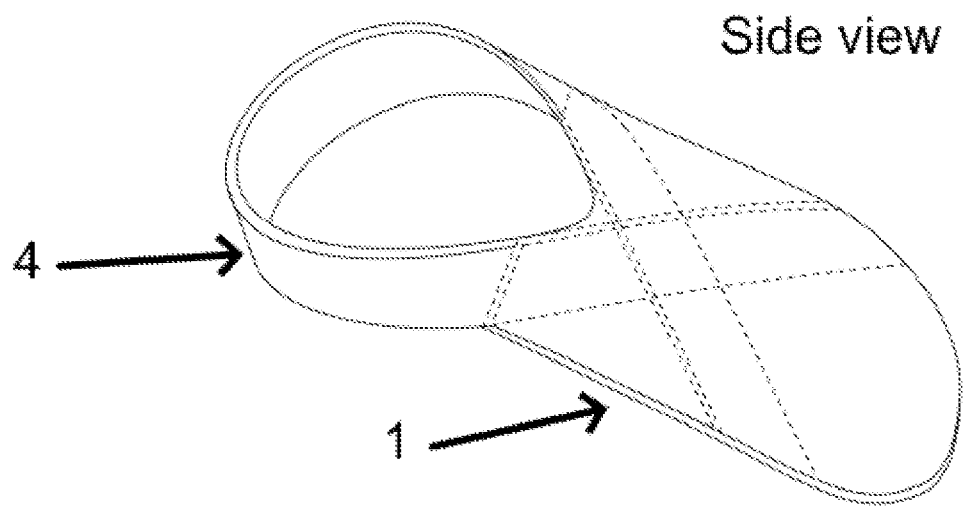
FIG. 1 is an oblique view of an exemplary bandage in accordance with the present disclosure.

Various modifications and adaptations of the exemplary bandage described here are possible and expected, yet the fundamental embodiment of the disclosure will be depicted in the drawings and described here in detail. Modifications, additions and adaptations to this disclosure will be described in the submitted claims.

DESCRIPTION OF THE INVENTION

This disclosure describes a bandage meant to cover the first knuckle or its pad on hands or feet. This disclosure concentrates on the shape and novelty of this bandage rather than any claim to unique materials or processing. This bandage has a continuous loop in place of any adhesive tabs or strings used to hold a bandage pad in place by winding around a digit. A continuous loop around a digit anchoring a pad has no sharper curve and needs no adhesive. Its material strength, not any adhesive properties, provides tension to hold a bandage pad in place and resist bandage pad peeling. Anatomically, the first joint on both the hand and foot has tissue extending away from the limb such that an anchor point around a digit is located further down the digit. This distance and thus the loop's size varies in length due to the many factors that shape the human physique. Two solutions offered here are rigid loops in various sizes, like clothing, or an adjustable loop made of a deformable material. The width and thickness of the loop is a compromise of flexibility, comfort and strength—flexibility to reduce loop creases or buckling around a digit, comfort to avoid skin irritations and hampering digit motions and strength to counteract peeling forces on the associated edge of the bandage. The bandage disclosed may be made of any currently available materials suitable for this desired use; to be water or tear resistant, water proof, breathable, radio-opaque, pharmaceutically active, etc. in any utilized layers. This disclosure concentrates on the shape and utility of this bandage due to the use of a single digit as anchor rather than any claim to unique materials or processing.

FIG. 1 is an oblique view of an exemplary bandage in accordance with the present disclosure. A top side pad 1 of the bandage and a digit loop 4 are visible. The loop 4 is angled with respect to the plane of the top side pad 1 and blended into the junction with top side pad 1 rather than an abrupt edge which may be a stress riser or abrasion point. The phantom lines of the loop 4 into the top side pad 1 suggest the loop 4 may need to be extended into the top side pad 1 material for loop strength, or the loop may be terminates at the edge of the top side pad 1 material.

Figure 2:
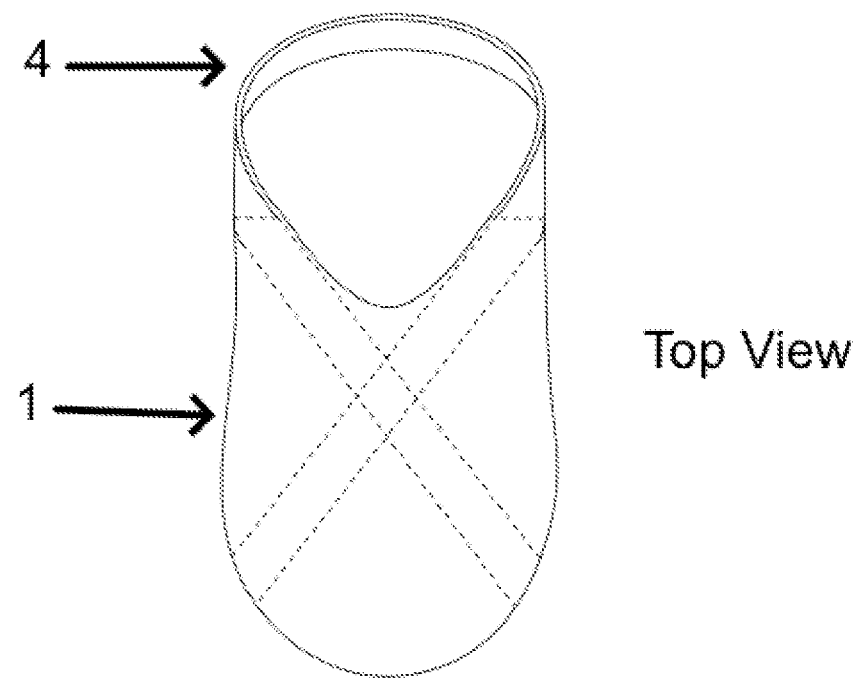
FIG. 2 is an outer-facing surface or top-side view of an exemplary bandage in accordance with the present disclosure.

FIG. 2 depicts the exemplary bandage and the default smooth shape of the top side pad 1. The pad is shaped to both cover a wound, create a smooth circumference around a digit and to meet the two edges of the digit loop 4. The same phantom lines of extended digit loop 4 are shown. Since the sterile portion of the bandage, the (bottom side pad 2), is directly below the top side pad 1 and is identical or less in area, the shape and area of the top side of the bandage defines the shape for the entire bandage pad.

Figure 3:
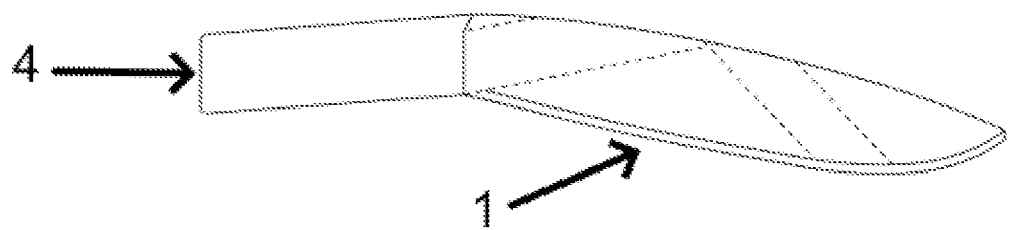
FIG. 3 is a side view of an exemplary bandage in accordance with the present disclosure.

FIG. 3 is a side view of the exemplary bandage with the digit loop 4 and the top side pad 1, specifically showing the angling between the two parts, in accommodation of typical body shapes near digits. The phantom digit loop 4 lines are drawn for clarity and perspective.

Figure 4:
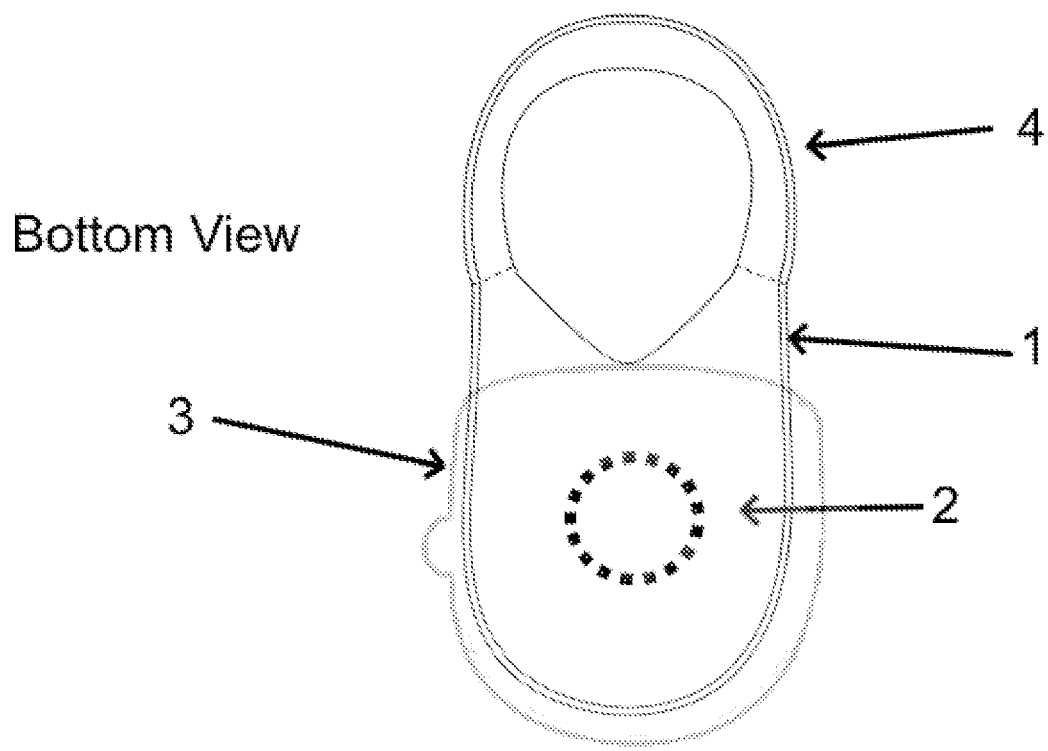
FIG. 4 is a skin-facing surface or bottom-side view of an exemplary bandage in accordance with the present disclosure.

FIG. 4 is a bottom view of the exemplary bandage, showing the orientation of the digit loop 4, the bottom side pad 2, and the temporary sterile pad cover 3. Bottom side 2 must contain the medicinal bandage area (if any) and the adhesive perimeter for the bandage. The phantom lines of the digit loop 4 have been omitted for clarity.

The first embodiment is an anti-abrasion/grip/blister pad—used to lessen the effects of friction and rubbing. The top side pad 1 surface is scuff and tear resistant, the bottom side pad 2 surface contains an adhesive and the digit loop 4 is either a sized or a deformable anchoring member.

The second embodiment is the traditional bandage, meant to cover, protect and help heal a wound. The top side pad 1 surface comprises suitable materials for the particular bandage and its features, the bottom side pad 2 surface of the bandage pad by necessity consists of at least two areas—an inner dressing area for the actual bandage material(s) and a perimeter adhesive circumference to seal and adhere the bottom side pad 2 surface to the skin. For any size bandage pad, the choice of side 2 materials and area are a balance between wound-covering material and sufficient adhesive area. The digit loop 4 is either a sized or a deformable anchoring member.

The third embodiment emphasizes the structure, shape and adhesion of a reinforced, three-dimensional shield. In this embodiment, the shape of the bandage and portions of all surfaces may vary: the top side pad 1, the bottom side pad 2 and the digit loop 4 may contain unique qualities such as conformal and thermal shaping, shape memory, perforations, and optical patterns, medical components, antennas, sensors or x-ray/ultrasound/RFID components. The digit loop 4 is again either a sized or a deformable anchoring member.

These and other embodiments require the same actions for use: a bandage of approximate digit loop size (the length from wound site, around digit, back to site) and sufficient pad surface area is placed over the digit, sterile pad cover still in place, to check where the dressing will touch. If over the wound, peel the sterile pad cover off and apply the bandage. If short, either replace with a longer size or pull on the top of the bandage to stretch the loop enough to center the dressing over the intended wound site before applying. If too long, replace with a shorter bandage that fits. Then peel the sterile pad cover off and apply the bandage.

What is claimed is:

1. A bandage comprising:
    a pad having a contoured perimeter size, a top outer surface, an inner skin surface and a designated bottom end;
    a loop of material that connects across the bottom end of the pad; and
    a sized protective release layer compatible with materials used on the inner skin surface and intended to protect them until used;
    wherein the inner skin surface of the pad is configured to be adhered to a location on the skin and the loop is configured to wrap around a digit near that location.

2. The bandage of claim 1, wherein the loop comprises a flexible, deformable material.

3. The bandage of claim 1, wherein the loop is free of adhesive.

4. The bandage of claim 3, further comprising an anti-friction component as the outer top surface of the pad and an adhesive applied to the inner skin surface of the pad.

5. The bandage of claim 3, further comprising a dressing coupled to an area on the inner skin surface of the pad, wherein the remainder of the area on the inner skin surface of the pad comprises an adhesive.

6. The bandage of claim 5 wherein the dressing includes other medical components appropriate for application to the location.

7. The bandage of claim 3, further comprising a sensor component for application to the location.

8. The bandage of claim 3, further comprising a reinforced top side pad surface.

\* \* \* \* \*